United States Patent [19]

Lorenz et al.

[11] 4,178,303

[45] Dec. 11, 1979

[54] (2-CYANO-3,3-DIPHENYLACRYLOXY) ALKYLENE ACRYLIC ACID ESTERS

[75] Inventors: Donald H. Lorenz, Basking Ridge; Bruce A. Gruber, Bloomingdale, both of N.J.

[73] Assignee: GAF Corporation, New York, N.Y.

[21] Appl. No.: 6,787

[22] Filed: Jan. 26, 1979

[51] Int. Cl.² ............................................. C07C 121/70
[52] U.S. Cl. .............................. 260/465 D; 526/264; 526/297; 526/323; 252/300
[58] Field of Search ..................................... 260/465 D

[56] References Cited

U.S. PATENT DOCUMENTS

| | | | |
|---|---|---|---|
| 3,215,724 | 11/1965 | Strobel et al. | 260/465 D |
| 3,573,216 | 3/1971 | Strobel et al. | 260/465 D |
| 3,644,466 | 2/1972 | Strobel et al. | 260/465 D |
| 3,993,684 | 11/1976 | Dunnavant et al. | 260/465 D X |

*Primary Examiner*—Dolph H. Torrence
*Attorney, Agent, or Firm*—Walter C. Kehm; Walter Katz

[57] ABSTRACT

This invention relates to copolymerizable ultraviolet light absorber compounds having the formula:

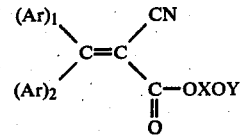

where
(Ar)$_1$ and (Ar)$_2$ are aromatic carbocylic nuclei of the benzene and naphthalene series and are independently selected from phenyl or phenyl substituted with alkyl, halo, alkoxy, carboxy, carbalkoxy, cyano, acetyl, benzoyl, phenyl, alkyl phenyl, phenoxy phenyl, alkyl substituted phenoxy, or alkoxy phenyl substituted phenyl, and naphthyl;

X is alkylene, C$_2$–C$_{17}$, unsubstituted or substituted with halo, cyano, alkyl C$_1$–C$_6$, alkoxy C$_1$–C$_6$, alkoxyalkyl C$_1$–C$_6$ or alkoxyalkyleneoxy C$_1$–C$_6$; and, Y is a copolymerizable radical selected from acryloyl C$_3$–C$_{12}$, alkylacryloyl C$_3$–C$_{12}$, acryloxyalkyl C$_3$–C$_{12}$, acryloxyhydroxyalkyl C$_3$–C$_{12}$ and alkylacryloxyhydroxyalkyl C$_3$–C$_{12}$.

11 Claims, No Drawings

(2-CYANO-3,3-DIPHENYLACRYLOXY) ALKYLENE ACRYLIC ACID ESTERS

BACKGROUND OF THE INVENTION

1. Field of the Invention

This invention relates to novel copolymerizable ultraviolet light absorber compounds, and, more particularly, to 2-cyano-3,3-diphenylacryloxy acrylic acid ester compounds which are copolymerizable with vinyl monomers to provide polymer materials having improved resistance to degradation to light.

2. Description of the Prior Art

Various organic compounds exhibit the power to absorb electromagnetic radiation and can be incorporated in various plastic materials such as transparent sheets which act as filters for all the radiation passing through and will transmit only such radiations as are not absorbed by the sheet and/or the absorbing agent. Such filters find use in many technical and commercial applications.

Numerous cyano acrylic compounds have been suggested as absorbents for the range of radiations described above. For specific compounds, see U.S. Pat. Nos. 3,081,280; 3,272,810; 3,644,466; 3,256,312 and 3,215,724. These ultra-violet absorbers are mechanically mixed with the plastic materials to prevent discoloration and degradation of the material. However, it has been observed that such absorbers sometimes fail or are blocked out of the plastic under adverse weather conditions before the lifetime of the protected material. Also, it is not possible to use all of these ultra-violet absorbers with radiation curing of the plastic material. Another disadvantage of these ultra-violet absorbers is the high amount of absorber needed for protection of some materials.

Accordingly, it is an object of the present invention to provide novel copolymerizable ultraviolet light absorber compounds which are substantially free of the disadvantages of the prior art.

A particular object of this invention is to provide novel compounds which can be copolymerized directly with the plastic material to provide more permanent ultraviolet light protection.

A specific object is to provide ultraviolet light absorber compounds containing a copolymerizable acryloyl group.

These and other objects and features of the invention will be made apparent from the following more particular description of the invention.

SUMMARY OF THE INVENTION

What is provided herein are improved, novel copolymerizable ultraviolet light absorber compounds of the formula:

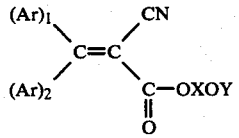

where
(Ar)$_1$ and (Ar)$_2$ are aromatic carbocyclic nuclei of the benzene and naphthalene series and are independently selected from phenyl or phenyl substituted with alkyl, halo, alkoxy, carboxy, carbalkoxy, cyano, acetyl, benzoyl, phenyl, alkyl phenyl, phenoxy phenyl, alkyl substituted phenoxy, or alkoxy phenyl substituted phenyl, and naphthyl;

X is alkylene, C$_2$–C$_{17}$, unsubstituted or substituted with halo, cyano, alkyl C$_1$–C$_6$, alkoxy C$_1$–$_{C6}$, alkoxyalkyl C$_1$–C$_6$ or alkoxyalkyleneoxy C$_1$–$_{C6}$; and Y is a copolymerizable radical selected from acryloyl C$_3$–C$_{12}$, alkylacryloyl C$_3$–C$_{12}$, acryloxyalkyl C$_3$–C$_{12}$, acryloxyhydroxyalkyl C$_3$–C$_{12}$ and alkylacryloxyhydroxyalkyl C$_3$–C$_{12}$.

In the best mode of the invention, (Ar)$_1$ and (Ar)$_2$ are phenyl, X is —C$_2$H$_4$— and Y is acryloyl or methacryloyl.

DETAILED DESCRIPTION OF THE INVENTION

Suitable (Ar)$_1$ and (Ar)$_2$ groups are given in U.S. Pat. No. 3,644,466, including representative starting benzophenone compounds. In the best mode of the invention, both (Ar)$_1$ and (Ar)$_2$ are phenyl.

The X groups are unsubstituted or substituted alkylene radicals, C$_2$–C$_{17}$. The preferred groups are unsubstituted lower alkylene, C$_2$–C$_6$, which are derived synthetically from ethylene glycol, propylene glycol, butanediol, and the like. The best mode is represented by —CH$_2$—CH$_2$—.

The Y radical is copolymerizable with vinyl monomers so that the ultraviolet absorber becomes an integral part of the polymer. Suitable Y groups are derived from acryloyl, alkylacryloyl, acryloxyalkyl, acryloxyhydroxyalkyl and alkylacryloxyhydroxyalkyl, wherein each is C$_3$–C$_{12}$. The preferred groups are acryloyl, methacryloyl, glycidyl acryloyl and glycidyl methacryloxyl. The best mode is represented by acryloyl or methacryloyl.

The compounds of the invention contain ultraviolet light absorber and copolymerizable portions in the same molecule. These portions are effectively separated by the X radical so that each can perform its own function without interference from the other. Therefore, the absorber portion does not inhibit the copolymerization, and the Y radical does not affect the light absorbing properties of the molecule.

The novel compounds of the invention may be prepared by esterification of 2-hydroxyalkyl(2-cyano-3,3-diphenyl) acrylate with an acryloyl halide or acrylic acid (Method 1) or by direct Knoevenagel condensation of a benzophenone with an acryloxyalkyl cyanoacetate (Method 2).

In Method 1, the hydroxy group of a hydroxyalkyl cyano acetate first is protected by acylation with a group convertible by hydrolysis to the hydroxy compound, e.g., with acetyl chloride, to provide the corresponding acetoxyalkyl cyanoacetate. The protected compound then is condensed with a benzophenone in a Knoevenagel reaction to provide the acetoxyalkyl(2-cyano-3,3-diphenyl) acrylate in good yield. Subsequent acid hydrolysis of the protecting acetyl group affords the corresponding hydroxy intermediate, which is then directly esterified with a suitable acryloyl halide or acrylic acid to give the desired compounds.

This method is summarized below:

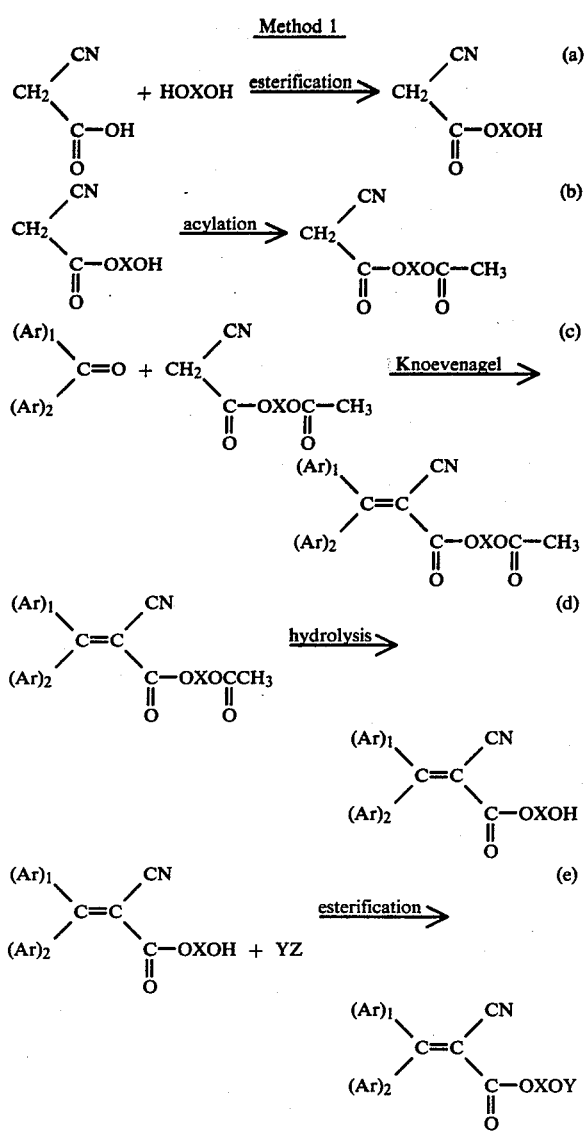

where Z is a halide or hydroxyl, and X and Y are as defined above.

Typical X groups are —CH₂CH₂, —CH₂CH₂CH₂—, —CH₂CH₂CH₂CH₂—, and the like.

Representative Y groups are

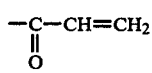

(acryloyl),

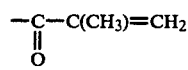

(methacryloyl),

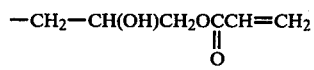

(3-acryloxy-2-hydroxypropyl), and

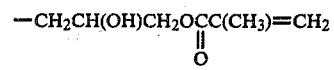

(3-methacryloxy-2-hydroxypropyl).

In step (a) of Method 1, cyanoacetic acid is reacted with a lower dihydric alcohol to form a hydroxyalkyl cyanoacetate, as described in U.S. Pat. No. 3,644,466, Example 3, cols. 7–8.

In step (b), the hydroxy group of the hydroxyalkyl cyanoacetate then is protected by acylation, suitably with acetic anhydride, to give the corresponding acetoxyalkyl cyanoacetate.

Step (c) in the process involves Knoevenagel condensation of a benzophenone with the acetoxyalkyl cyanoacetate. The Knoevenagel reaction is generally run in the presence of a solvent, such as benzene, toluene, or ethylenedichloride, under reflux, usually at a temperature between 80° and 100° C. for about 24 hours. The reaction preferably proceeds in a nitrogen atmosphere and in the presence of glacial acetic acid and ammonium acetate as a catalyst. Conventional washings of the product with water and saturated bicarbonate solution are done prior to the drying, removing the solvent, and recovering the product.

The fourth step (d) in the synthesis is to remove the protecting acetyl group by acid hydrolysis in alcohol to provide the corresponding free hydroxyalkyl compound. This step is carried out in methanol under acid conditions at reflux temperatures.

The final step (e) in Method 1 involves esterification with a reactive acryloyl compound, such as an acryloyl halide, e.g., acryloyl chloride or acryloyl bromide. The reaction is carried out in an inert solvent, suitably an aromatic or aliphatic hydrocarbon or halogenated hydrocarbon, such as toluene, benzene, chloroform or etylene dichloride, or in acetone, at a suitable temperature, generally ranging from room temperature to the reflux temperature of the solvent, e.g., if chloroform, at about 61° C., and in the presence of a base, such as sodium bicarbonate, to absorb the acid by-product of the reaction. Suitably the molar ratios of the reactants are controlled to provide at least a 1:1 molar ratio of the acryloyl halide to the hydroxyalkyl(2-cyano-3,3-diphenyl) acrylate. Preferably an excess of the acryloyl chloride is used. The reaction is run for about 1–5 hours at the reflux temperature.

The yield of product in step (c) in Method 1 is about 80–90%.

An acrylic acid may be used in place of an acryloyl chloride in step (e). In this embodiment, water is distilled out of the reaction mixture as an azeotrope with the solvent. Preferably, an inhibitor, such as phenothiazine or methoxyphenol, is included in the reaction mixture in an amount of about 200–1000 ppm to prevent polymerization of the acrylic acid reactant. The reaction with acrylic acid generally is run at a somewhat higher temperature than with the acryloyl chloride, usually at about 80° 110° C., for about 10 to about 20 hours. The yields are about 60–70%.

In Method 2, a hydroxyalkyl cyanoacetate is reacted first with an acryloyl chloride or acrylic acid to form a 2-acryloxyalkyl 2-cyanoacetate intermediate. Then the intermediate is condensed directly with a benzophenone in the Knoevenagel reaction to form the desired compounds, as follows:

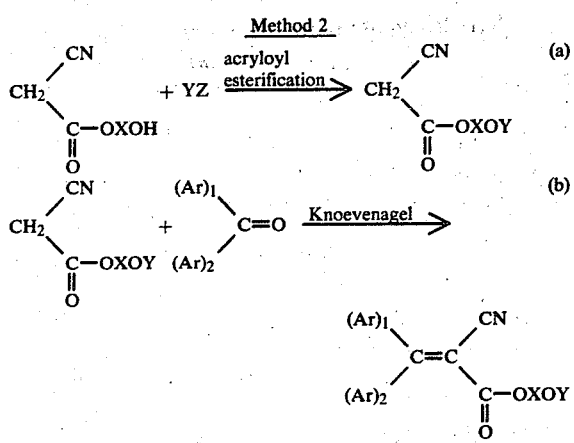

where X, Y and Z are as defined above.

The reaction conditions in steps (a) and (b) of Method 2 correspond generally to those described in steps (e) and (c) of Method 1, respectively.

The compounds of the invention may be copolymerized, for example, with a urethane oligomer, by radiation curing, to provide useful polymeric coatings.

The following examples will describe the invention with more particularity.

EXAMPLE 1

2-(2-Cyano-3,3-Diphenylacryloxy) Ethyl Acrylate

Method 1

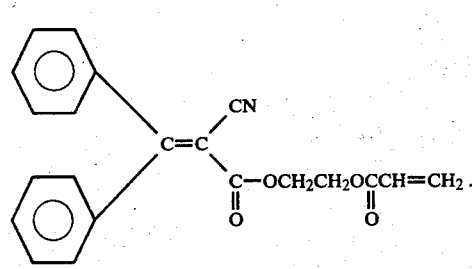

(a) 2-Hydroxyethyl 2-Cyanoacetate

Cyanoacetic acid was esterified with ethylene glycol according to U.S. Pat. No. 3,644,466 (col. 7-8, Ex. 3) to give the product in 74% yield.

(b) 2-Acetoxyethyl 2-Cyanoacetate

Into a three-neck round bottom flask with magnetic stirrer, dropping funnel, thermometer, and drying tube was charged 122 g. (1.2 moles) of acetic anhydride and 10 drops of concentrated sulfuric acid. Then 129 g. (1 mole) of 2-hydroxyethyl cyanoacetate was added dropwise with stirring while maintaining the reaction temperature below 75° C. The acylated ester thus produced was then diluted with 100 ml. of water and the excess acid was neutralized with solid potassium carbonate. The oil layer was separated and dried to yield 130 g. (79%) of the desired compound.

(c) 2-Acetoxyethyl 2-Cyano-3,3-Diphenylacrylate

A three-neck round bottom flask fitted with a mechanical stirrer, a thermometer and a Dean-Stark trap fitted with a reflux condenser was charged with 200 ml. of toluene, 182 g. (1 mole) of benzophenone, 205 g. (1.2 moles) of 2-acetoxyethyl 2-cyanoacetate, 40 ml. of glacial acetic acid, 16 g. of ammonium acetate. The contents were heated to reflux (110° C.) for 24 hours while the theoretical amount of water by-product was removed by azeotropic distillation. Upon removal of the solvent, as well as unreacted starting material by vacuum distillation, a yield of 200 g. (60%) of the desired product was obtained.

(d) 2-Hydroxyethyl 2-Cyano-3,3-Diphenylacrylate

A charge of 800 ml of methanol, 355 g. (1 mole) of 2-acetoxyethyl 2-cyano-3,3-diphenylacrylate and 10 drops of concentrated hydrochloric acid was heated at 65° C. for 18 hours. Evaporation of the solvent left 235 g. (80%) of the intermediate compound as an amber, viscous oil.

(e) 2-(2-Cyano-3,3-Diphenylacrylate)Ethyl Acrylate

To a charge of 3 l. of methylene chloride, 179 g. of potassium carbonate and 293 g. (1 mole) of 2-hydroxyethyl 2-cyano-3,3-diphenylacrylate was added 118 g. (1.3 moles) of acryloyl chloride and the contents were heated at 41° C. for 2 hours. The reaction mixture then was diluted with 3 l. of water and neutralized with solid potassium carbonate. The organic layer was separated, dried and evaporated, leaving 274 g. (79%) of an amber oil, which was characterized by NMR as the product compound.

EXAMPLE 2

The compound of Example 1 was prepared using acrylic acid instead of acryloyl chloride in Step (e) of Example 1 as follows:

(e) A charge of 347 g. (1 mole) of 2-hydroxyethyl 2-cyano-3,3-diphenylacrylate in 1.5 l. of toluene was heated at reflux (110° C.) to remove residual water and the solution was cooled to 30° C. Then 96 g. (1.3 moles) of acrylic acid, 5 g. of p-toluene sulfonic acid and 350 mg. of phenothiazine was added and the solution was heated at reflux for 16 hours. The reaction mixture then was cooled to room temperature and 1 l. of water was added and the solution was neutralized with solid potassium carbonate. The organic layer then was dried and evaporated to yield 328 g. (80% yield, about 75% purity) of an amber oil of the product compound.

EXAMPLE 3

2-(2-Cyano-3,3-Diphenylacryloxy) Ethyl Methacrylate

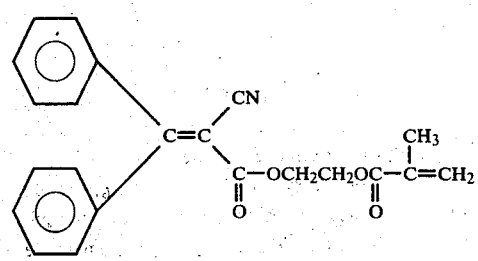

Using an equivalent amount of methacryloyl chloride in place of acryloyl chloride in Step (e) of Example 1, the desired ethyl methacrylate compound is obtained in comparable yield.

EXAMPLE 4

3-(2-Cyano-3,3-Diphenylacryloyl) Propyl Methacrylate

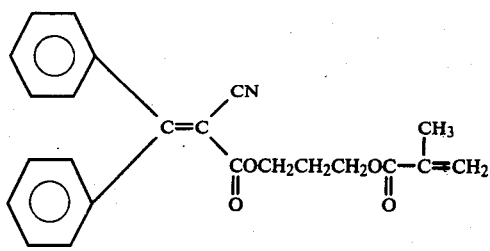

Using an equivalent amount of propylene glycol in place of ethylene glycol in Step (a) in Example 3, there is produced the desired propylmethacrylate compound in comparable yield.

EXAMPLE 5

4-(2-Cyano-3,3-Diphenylacryloyl) Butyl Acrylate

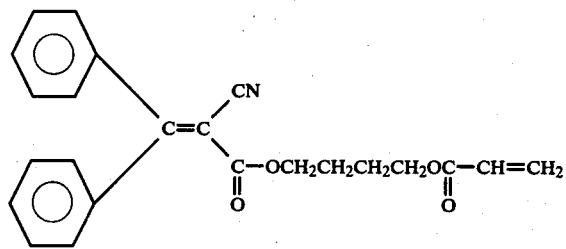

By substituting 1,4-butanediol in place of ethylene glycol in Step (a) of Example 1, there is produced the corresponding butyl acrylate.

EXAMPLE 6

2-Hydroxy-3-[2-(2-Cyano-3,3-Diphenyl) Ethoxy]Propyl Acrylate

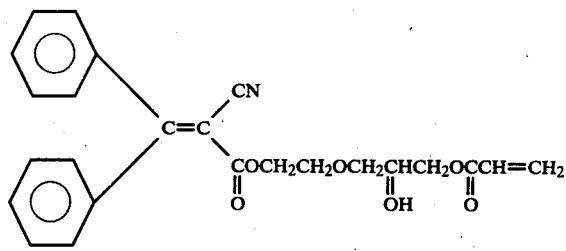

The procedure of Example 1 is followed except for (e) as follows:

Into a round bottom flask is charged 29.3 g. (0.1 mole of 2-hydroxyethyl 2-cyano-3,3-diphenylacrylate, 21.3 g. (0.15 mole) glycidyl acrylate and 0.27 g. (0.0025 mole) tetramethylammonium chloride. The mixture was heated at 70°-90° for 5 hours. Thereafter excess glycidyl acrylate was removed by vacuum distillation. The remaining amber oil was the desired ethoxy propyl acrylate product.

EXAMPLE 7

2-Hydroxy-3-[2-(2-Cyano-3,3-Diphenylacryloxy) Ethoxy]Propyl Methacrylate

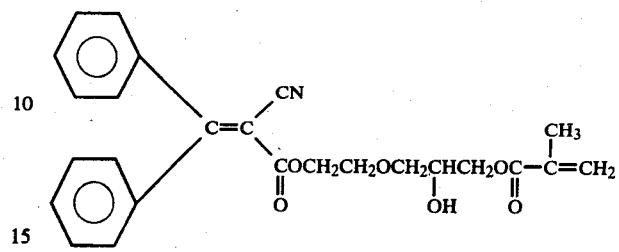

Using glycidyl methacrylate in place of glycidyl acrylate in Example 6 gives the corresponding methacrylate compound.

EXAMPLE 8

2-(2-Cyano-3,3-Diphenylacryloxy) Ethyl Acrylate (Method 2)

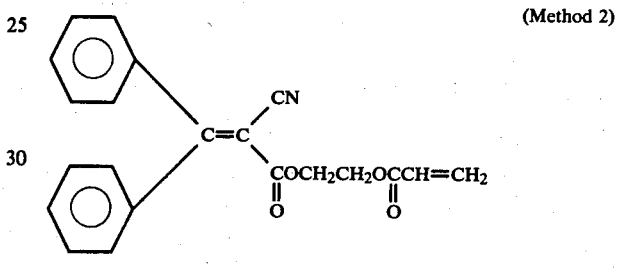

A. Acryloxyethyl 2-Cyanoacetate

Into a flask fitted with a mechanical stirrer and a reflux condenser is charged 1 l. of methylene chloride 129 g. (1 mole), 2-hydroxyethyl 2-cyanoacetate 118 g. (1.3 moles), acryloyl chloride and 179 g. potassium carbonate. The reaction mixture was heated at reflux (41° C.) for 2 hours, diluted with 1 l. of water and neutralized with solid potassium carbonate. The organic layer then was separated, dried and evaporated leaving 128 g. (70%) of 2-acryloxyethyl 2-cyanoacetate, which was stabilized with 50 ppm of hydroquinone.

(b) In a round bottom flask equipped with a mechanical stirrer, a thermometer, and a Dean-Stark water trap fitted with a reflux condenser was charged 270 ml. toluene, 182 g. (1 mole) of benzophenone, 183 g. (1 mole) of 2-acryloxyethyl 2-cyanoacetate, 26 mg. of phenothiazine, 50 ml. of glacial acetic acid, and 20 g. of ammonium acetate. The solution then was heated at reflux (110° C.) for 16 hours. After cooling, the reaction solution was washed with 300 ml. of water and the organic layer was separated and dried. The toluene solvent was evaporated leaving an amber oil which was predominantly the product compound.

EXAMPLE 9

Preparation of Radiation Cured Coating

Into a dry 1 l. resin kettle fitted with an air inlet tube, a stirrer, thermometer, and dropping funnel was charged 300.8 g. (1.3 moles) of isophorone diisocyanate and 4.8 ml. of a 10% (W/V) solution of dibutyltin dilaurate catalyst in ethylhexylacrylate. Dry air then was bubbled through the stirred solution while 322.1 g. (0.61 moles) of polyolcaprolactone (PCP-200) was added dropwise over 45 minutes. The solution then was heated to 80° C. and the reactants maintained at this temperature for 30 minutes. After cooling to 55° C., 160 mg. of phenothiazine was admixed. Then 151.9 g. (1.3 moles) of hydroxyethyl acrylate was added rapidly. The temperature was raised to 80° C. and maintained for 2 hours.

The resulting oligomer (58.1 g.) was formulated for coating by mixing with 25.4 g. of ethylhexylacrylate, 16.8 g. of vinyl pyrrolidone, 14.2 g. of hexanediol diacrylate, 1.8 g. of DC-193 silicone surfactant, 2.4 g. of Vicure-10 photoinitiator and 2.5 g. of 2-(2-cyano-3,3-diphenylacryloxy) ethyl acrylate. The resulting syrup was coated onto a polyvinylchloride plate to form a film having a thickness of 1.5 mil. The film then was cured by ultraviolet radiation under an inert atmosphere to provide a tough, clear coating containing the copolymerized UV absorber compound of the invention.

While certain preferred embodiments of the present invention have been illustrated by way of specific example it is to be understood that the present invention is in no way to be deemed as limited thereto but should be construed as broadly as all or any equivalents thereof.

What is claimed is:

1. Copolymerizable ultraviolet light absorber compounds having the formula:

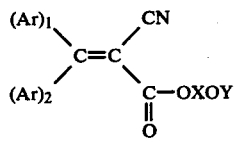

where
(Ar)$_1$ and (AR)$_2$ are aromatic carbocyclic nuclei of the benzene and naphthalene series and are independently selected from phenyl or phenyl substituted with alkyl, halo, alkoxy, carboxy, carbalkoxy, cyano, acetyl, benzoyl, phenyl, alkyl phenyl, phenoxy phenyl, alkyl substituted phenoxy, or alkoxy phenyl substituted phenyl, and naphthyl;
X is alkylene, $C_2$-$C_{17}$, unsubstituted or substituted with halo, cyano, alkyl $C_1$-$C_6$, alkoxy $C_1$-$C_6$, alkoxyalkyl $C_1$-$C_6$ or alkoxyalkyleneoxy $C_1$-$C_6$; and,
Y is a copolymerizable radical selected from acryloyl $C_3$-$C_{12}$, alkylacryoyl $C_3$-$C_{12}$, acryloxyalkyl $C_3$-$C_{12}$, acryloxyhydroxyalkyl $C_3$-$C_{12}$ and alkylacryloxyhydroxyalkyl $C_3$-$C_{12}$.

2. Compounds according to claim 1 in which both (Ar)$_1$ and (Ar)$_2$ are phenyl.

3. Compounds according to claim 1 in which X is alkylene, $C_2$-$C_6$.

4. Compounds according to claim 1 in which Y is acryloyl, methacryloyl, 3-acryloxy-2-hydroxypropyl or 3-methacryloxy-2-hydroxypropyl.

5. Compounds according to claim 1 in which both (Ar)$_1$ and (Ar)$_2$ are phenyl, X is alkylene, $C_2$-$C_6$ and Y is acryloyl, methacryloyl, 3-acryloxy-2-hydroxypropyl or 3-methacryloxy-2-hydroxypropyl.

6. A compound according to claim 1 which is 2-(2-cyano-3,3-diphenylacryloxy) ethyl acrylate.

7. A compound according to claim 1 which is 2-(2-cyano-3,3-diphenylacryloxy) ethyl methacrylate.

8. A compound according to claim 1 which is 3-(2-cyano-3,3-diphenylacryloxy) propyl acrylate.

9. A compound according to claim 1 which is 4-(2-cyano-3,3-diphenylacryloxy) butyl acrylate.

10. A compound according to claim 1 which is 3-(2-cyano-3,3-diphenylacryloyloxy)-2-hydroxypropyl acrylate.

11. A compound according to claim 1 which is 3-(2-cyano-3,3-diphenylacryloyloxy)-2-hydroxypropyl methacrylate.

* * * * *